(12) United States Patent
Atherton et al.

(10) Patent No.: US 7,078,059 B2
(45) Date of Patent: Jul. 18, 2006

(54) TREATMENT OF BONE DISEASES

(75) Inventors: Nigel D. Atherton, Hampshire (GB); Joseph William Totten, Hampshire (GB); Michael David Gaitonde, Binningen (CH)

(73) Assignee: Shire Holdings AG, Zug (CH)

( * ) Notice: Subject to any disclaimer, the term of this patent is extended or adjusted under 35 U.S.C. 154(b) by 9 days.

(21) Appl. No.: 09/891,206

(22) Filed: Jun. 26, 2001

(65) Prior Publication Data
US 2002/0051822 A1 May 2, 2002

(30) Foreign Application Priority Data
Jun. 27, 2000 (GB) .............................................. 0015745

(51) Int. Cl.
*A61K 33/24* (2006.01)
*A61K 31/28* (2006.01)
*A61P 19/02* (2006.01)
*A61P 19/08* (2006.01)
*A61P 19/10* (2006.01)

(52) U.S. Cl. ...................... 424/617; 424/600; 424/667; 424/673; 424/676; 424/677; 424/682; 424/702; 424/715; 424/722; 424/DIG. 6; 514/2; 514/12; 514/102; 514/107; 514/108; 514/114; 514/167; 514/168; 514/169; 514/170; 514/171; 514/182; 514/184; 514/185; 514/186; 514/187; 514/188; 514/324; 514/460; 514/492; 514/533; 514/648; 514/825; 514/836; 514/900

(58) Field of Classification Search ................ 424/600, 424/617, 667, 673, 676, 677, 682, 702, 715, 424/722, DIG. 6; 514/2, 12, 102, 107, 108, 514/114, 167–171, 182, 184–188, 324, 460, 514/492, 533, 648, 825, 836, 900
See application file for complete search history.

(56) References Cited

U.S. PATENT DOCUMENTS

| 5,342,604 | A | 8/1994 | Wilson et al. | |
| 5,714,631 | A | 2/1998 | Wilson et al. | |
| 5,902,825 | A | 5/1999 | Jia | |
| 5,968,976 | A | 10/1999 | Murrer et al. | |
| 6,027,737 | A | 2/2000 | Morris, Jr. et al. | |
| 2004/0082588 | A1 * | 4/2004 | Evans et al. | ............ 514/253.03 |
| 2005/0079135 | A1 * | 4/2005 | Haslam et al. | ............... 424/9.3 |

FOREIGN PATENT DOCUMENTS

| FR | 2 493 704 | 11/1980 |
| WO | WO 96/30029 | 10/1996 |

OTHER PUBLICATIONS

DRUGU abstract, accession No. 1987–06492; abstracting Singh et al., Curr. Sci., vol. 55, No. 17, pp. 846–848 (1986).*
'Renal Osteodystrophy'. National Institute of Diabetes and Digestive and Kidney Diseases [online]. Posted May 2001 [retrieve on Jan. 24, 2003]. Retrieved from the Internet: <URL: www.niddk.nih.gov/healthykidney/pus/kidney–failure/renal– osteodystrophy.htm.*
Fernandez–Gavarron et al., "Incorporation of 140–lanthanum into bones, teeth and hydroxyapatite", *Bone and Mineral 3*, 1998, pp. 283–291.
Yanagihara et al., "Synthesis of Lanthanide Carbonates", *Journal of the Less–Common Metals*, 167: 1991, pp 223–232.
Guggino et al., "Bone remodeling signaled by a dihydropyridine– and phenylalkylamine–sensitive calcium channel", *Proc. Natl. Acad. Sci.*, 86:Apr. 1999, pp. 2957–2960.
Graff et al., "A Possible Non–aluminum oral phosphate binder? A Comparative Study on Dietary Phosphorus Absorption", *Research Communications in Molecular Pathology and Pharmacology*, Sep. 1995, pp, 373–388, vol. 89, No. 3.
Hergesell et al., Phosphate binders on iron basis: A new perspective?, *Kidney International*, 1999, pp. S–42–S–45, vol. 56., Suppl. 73.
Hutchison et al., "Calcitrol, Lanthanum carbonate, and other new phosphate binders in the management of renal osteodystrophy", *Procedings of the ISPD '98—The VIIIth Congress of the ISPD*, Aug. 28–26, 1998, pp. S408–S412.
J. McClure et al., "The production of Calcification in connective Tissue and Skeletal Muscle Using Various Chemical Compounds", *Calicif Tiss. Res.*, 22: 1976, pp. 129–135.
Shankar et al., Activation and inactivation of the osteoclast $Ca^{2+}$receptor by the trivalent cation, $La^{3+}$, *Biochemicaland Biophysical Research Communications*, 187 (2): Sep. 16, 1992, pp 907–912.
Zimmermann et al., "Inhibition of chondrogenesis and endochrondral mineralization in vitro by different calcium channel blockers", *European Journal of Cell Biology*, 1994, pp. 114–121, vol. 63.
Harris et al., "The Effect of Lanthanum Chloride and related Compounds on Calcification", *Arch. int. Pharmacodyn.* 1970, pp. 269–278, vol. 186.
Doty et al., "Morphological Evidence of gap Junctions Between Bone Cells", *Calcif. Tissue Int.*, 1981, pp 509–512, vol. 33.

(Continued)

Primary Examiner—John Pak
(74) Attorney, Agent, or Firm—Darby & Darby (57) ABSTRACT

The invention provides a method for enhancing bone formation, inhibiting osteoclastic differentiation and/or activating osteoblastic differentiation whereby to manage, treat or achieve prophylaxis of bone disease which comprises administering to a human or animal subject suffering from, or susceptible to bone disease a therapeutically or prophylactically effective amount of a lanthanum compound.

44 Claims, 2 Drawing Sheets

OTHER PUBLICATIONS

R.H. Wasserman et al., "Effect of Vitamin $D_3$ on Lanthanum Absorption: Suggestive Evidence for a Shunt Path", *Calcium Metab. Bone Metab., Bone Dis., Proc. Eur. Symp. Calcif. Tissues 10$^{th}$*, 1975, pp. 87–90.

International Search Report dated May 17, 2002.

Evans, C.H ,"Chapter 8: *Toxicology and Pharmacology of the Lanthanides*", (1990) Biochemistry of the Lanthanides. Plenum Press, New York, NY, pp. 339–389.

Thomas J. Haley, "*Pharmacology and Toxicology of the Rare Earth Elements*", Journal of Pharmaceutical Sciences, vol. 54, No. 5 (1965), pp. 663–669.

Tandra Das et al., "*Effects of Lanthanum in Cellular Systems: A Review*" Biological Trace Element Research, vol. 18, (1988), pp. 201–228.

* cited by examiner

TREATMENT OF BONE DISEASES

This application claims priority to United Kingdom Application Serial No. 0015745.3, filed Jun. 27, 2000.

BRIEF DESCRIPTION OF THE INVENTION

This invention relates to the treatment and prevention of bone diseases, to methods of enhancing bone formation and also to the treatment of bone fracture.

BACKGROUND OF THE INVENTION

Throughout life, old bone is continuously removed by bone-resorbing osteoclasts and replaced with new bone which is formed by osteoblasts. This cycle is called the bone-remodelling cycle and is normally highly regulated, i.e. the functioning of osteoclasts and osteoblasts is linked such that in a steady state the same amount of bone is formed as is resorbed.

The bone-remodelling cycle occurs at particular areas on the surfaces of bones. Osteoclasts which are formed from appropriate precursor cells within bones resorb portions of bone; new bone is then generated by osteoblastic activity. Osteoblasts synthesise the collagenous precursors of bone matrix and also regulate its mineralization. The dynamic activity of osteoblasts in the bone remodelling cycle to meet the requirements of skeletal growth and matrix and also regulate its maintenance and mechanical function is thought to be influenced by various factors, such as hormones, growth factors, physical activity and other stimuli. Osteoblasts are thought to have receptors for parathyroid hormone and estrogen. Ostoeclasts adhere to the surface of bone undergoing resorption and are thought to be activated by some form of signal from osteoblasts.

Irregularities in one or more stages of the bone-remodelling cycle (e.g. where the balance between bone formation and resorption is lost) can lead to bone remodelling dirorders, or metabolic bone diseases. Examples of such diseases are osteoporosis, Paget's disease and rickets. Some of these diseases are caused by over-activity of one half of the bone-remodelling cycle compared with the other, i.e. by osteoclasts or osteoblasts. In osteoporosis, for example, there is a relative increase in osteoclastic activity which may cause a reduction in bone density and mass. Osteoporosis is the most common of the metabolic bone diseases and may be either a primary disease or may be secondary to another disease or other diseases.

Post-menopausal osteoporosis is currently the most common form of osteoporosis. Senile osteoporosis afflicts elderly patients of either sex and younger individuals occasionally suffer from osteoporosis.

Osteoporosis is characterised generally by a loss of bone density. Thinning and weakening of the bones leads to increased fracturing from minimal trauma. The most prevalent fracturing in post-menopausal osteoporotics is of the wrist and spine. Senile osteoporosis, is characterised by a higher than average fracturing of the femur.

Whilst osteoporosis as a therapeutic target has been of, and continues to, attract a great deal of interest, tight coupling between the osteoblastic and osteoclastic activities of the bone remodelling cycle make the replacement of bone already lost an extremely difficult challenge. Consequently, research into treatments for prevention or prophylaxis of osteoporosis (as opposed to replacement of already-lost bone) has yielded greater results to date.

Oestrogen deficiency has been considered to be a major cause of post-menopausal osteoporosis. Indeed steroids including oestrogen have been used as therapeutic agents (*New Eng. J. Med.*, 303, 1195 (1980)). However, recent studies have concluded that other causes must exist (*J. Clin. Invest.*, 77, 1487 (1986)).

Other bone diseases can be caused by an irregularity in the bone-remodelling cycle whereby both increased bone resorption and increased bone formation occur. Paget's disease is one such example.

Lanthanum has been of prominence previously in medicine on account of its property of forming stable complexes with phosphate. This application has been evidenced in the treatment of hyperphosphataemia by application of lanthanum carbonate. U.S. Pat. No. 5,968,976 describes the preparation and use in a pharmaceutical composition of certain hydrates of lanthanum carbonate for the treatment of hyperphosphataemia.

Fernandez-Gavarron et al. (*Bone and Mineral*, 283–291 (1988)) report on studies into the incorporation of 140-lanthanum into bones teeth and hydroxyapatite in vitro. Whilst the depth of uptake varied from an estimated 5 to 15 μm (dependent on experimental conditions), the authors' conclusion was that an exchange of lanthanum for calcium in hydroxyapatite may provide for increased resistance to acidic induced dissolution. Based on this suggested increased acid-resistance, the authors suggest that lanthanum's clinical usefulness as an adjunct in treating diseases such as osteoporosis, root caries and alveolar bone resorption might be explored.

Vijai S. Shankar et al. (Biochemical and Biophysical Research Communications, 907–912 (1992)) report that extracellular application of Lanthanum (III) induced a concentration-dependant elevation of cytosolic calcium in osteoclasts. The authors suggested that the osteoclast calcium receptor may be sensitive to activation and inactivation by the trivalent cation Lanthanum.

Bernd Zimmermann et al. (European Journal of Cell Biology, 114–121 (1994)) report that lanthanum inhibited endochondral mineralization and reduced calcium accumulation in organoid cultures of limb bud mesodermal cells.

SUMMARY OF THE INVENTION

We have surprisingly found that lanthanum (III) compounds enhance bone formation and bone density and have beneficial effects on the activity and differentiation of bone cells.

Accordingly, the present invention relates to a method for enhancing bone formation in a mammal in need thereof comprising administering to the mammal an effective amount of a lanthanum compound, preferably lanthanum (III). In accordance with an embodiment of the invention the mammal is a human. The human may have a bone deficit or be at risk of developing a bone deficit. The invention also contemplates that the human has a bone remodelling disorder or is at risk of developing such disorder. Examples of bone remodelling disorders include osteoporosis, Paget's disease, osteoarthritis, rheumatoid arthritis, achondroplasia, osteochodrytis, hyperparathyroidism, osteogenesis imperfecta, congenital hypophosphatasia, fribromatous lesions, fibrous displasia, multiple myeloma, abnormal bone turnover, osteolytic bone disease and periodontal disease.

In an embodiment the bone remodelling disorder is osteoporosis, including primary osteoporosis, secondary osteoporosis, post-menopausal osteoporosis, male osteoporosis and steroid induced osteoporosis.

Also provided is a method for enhancing bone formation in a mammal having a bone deficit which does not result from a bone remodelling disorder. Such bone deficits may result, for example, from a bone fracture, bone trauma, or a condition associated with post-traumatic bone surgery, post-prosthetic joint surgery, post-plastic bone surgery, post-dental surgery, bone chemotherapy treatment or bone radio-therapy treatment.

In an embodiment of the methods of the invention the lanthanum (III) compound is lanthanum chloride, lanthanum carbonate, lanthanum salts, chelates or derivatives thereof, lanthanum resins or lanthanum absorbants.

In a further embodiment of the methods of the invention, the effective amount of lanthanum (III) compound is from 0.01 mg/Kg/Day to 100 mg/Kg/Day, preferably from 0.05 mg/Kg/Day to 50 mg/Kg/Day or from 0.1 mg/Kg/Day to 10 mg/Kg/Day.

The present invention also provides a method for increasing bone density in a mammal in need thereof comprising administering to said mammal an effective amount of a lanthanum (III) compound. Also provided is a method for stimulating osteoblast differentiation by contacting the osteoblasts with an effective amount of lanthanum (III) compound thereby stimulating differentiation. Still further is provided a method for inhibiting osteoclast differentiation by contacting osteoclasts with an effective amount of lanthanum (III) compound thereby inhibiting differentiation.

In a further embodiment, the invention provides a method for activating the bone formation activity of differentiated osteoblasts by contacting the osteoblasts with an effective amount of lanthanum (III) compound thereby stimulating bone formation. The invention also contemplates a method for simultaneously stimulating osteoblast differentiation and inhibiting osteoclast differentiation in a mammal having a bone remodeling disorder, or being at risk of developing a bone remodeling disorder, by administering to the mammal an effective amount of lanthanum (III)compound.

The invention also contemplates a method for enhancing bone formation in a mammal in need thereof by administering to the mammal an effective amount of a lanthanum (III) compound and at least one bone enhancing agent. Examples of suitable bone enhancing agents include a synthetic hormone, a natural hormone, oestrogen, calcitonin, tamoxifen, a bisphosphonate, a bisphosphonate analog, vitamin D, a vitamin D analog, a mineral supplement, a statin drug, a selective oestrogen receptor modulator and sodium fluoride.

The invention further contemplates the use of a lanthanum III compound for the preparation of a medicament for use in enhancing bone formation in a mammal in need thereof. In an embodiment the mammal is a human having a bone remodelling disorder or being at risk of developing such disorder. In a further embodiment, the invention contemplates a pharmaceutical composition for the treatment or prevention of a bone remodelling disorder comprising a lanthanum (III) compound and a bone enhancing agent.

The present inventors have also found that lanthanum compounds may be used to inhibit selectively osteoclast differentiation. At certain low concentrations osteoblast differentiation may be activated and increased bone formation may result from the manifestation of either or both of these phenomena.

According to one aspect of the invention, there is thus provided a method for inhibiting osteoclastic differentiation whereby to manage, treat or achieve prophylaxis of bone disease which comprises administering to a human or animal subject suffering from, or susceptible to bone disease a therapeutically or prophylactically effective amount of a lanthanum compound.

Viewed from a further aspect there is provided a method for activating osteoblastic differentiation whereby to manage, treat or achieve prophylaxis of bone disease which comprises administering to a human or animal subject suffering from, or susceptible to bone disease a therapeutically or prophylactically effective amount of a lanthanum compound.

In this text, "susceptible to bone disease" is intended to embrace a higher than average predisposition towards developing bone disease. As an example, those susceptible towards osteoporosis include post-menopausal women, elderly males (e.g. those over the age of 65) and those being treated with drugs known to cause osteoporosis as a side-effect (e.g. steroid-induced osteoporosis).

According to a still further aspect of the invention there is provided the use of a lanthanum compound for the preparation of a medicament for use in any method of the invention.

According to a yet further aspect of the invention there is provided the use of a lanthanum compound in any method of the invention.

According to a yet further aspect of the invention there is provided the use of a lanthanum compound for the preparation of a pharmaceutical composition for use in the diagnosis of bone disease or of bone fracture.

These and other aspects of the invention will become evident upon reference to the following detailed description and attached drawings. In addition reference is made herein to various publications which are hereby incorporated by reference in their entirety.

BRIEF DESCRIPTION OF THE DRAWINGS

The invention will be better understood by reference to the following drawings in which.

DETAILED DESCRIPTION OF THE INVENTION

As hereinbefore mentioned, the present invention provides a method for enhancing bone formation in a mammal in need thereof comprising administering to said mammal an effective amount of a lanthanum compound, preferably a lanthanum (III) compound. Bone formation, or osteogenesis, refers to the creation of new bone mass. This includes the process whereby new bone structure grows or the density of existing bone is increased. Osteoblasts form bone by producing extracellular organic matrix, or osteoid and then mineralizing the matrix to form bone. The main mineral component of bone is crystalline hydroxyapetite, which comprises much of the mass of normal adult bone. The inventors have surprisinlgy found that lanthanum significantly enhances bone formation in vitro and in vivo. Enhanced bone formation in vitro was observed when lanthanum (III) was added to cultures of mature osteoblasts in vitro at concentrations of from 100 to 15,000 ng/ml. Enhanced bone formation was quantitated by measuring the amount of calcium incorporated into bone nodules formed by the osteoblasts.

The present inventors have also found that lanthanum (III) enhanced bone formation in growing dogs. A dose of 2,000 mg/kg/day lanthanum enhanced bone formation and produced a significant increase in bone volume and density compared to control animals.

Lanthanum (III) compounds may be used in the methods of the invention to enhance bone formation in a range of mammals, including domestic animals, such as pigs, cattle, horses, sheep and goats and also including pets and experimental mammals, such as dogs, cats and rodents.

In an embodiment of the invention the mammal is a human in need of enhanced bone formation. In one aspect, the human in need has a bone deficit, which means that they will have less bone than desirable or that the bone will be less dense or strong than desired. A bone deficit may be localised, such as that caused by a bone fracture or systemic, such as that caused by osteoporosis. Bone deficits may result from a bone remodelling disorder whereby the balance between bone formation and bone resorption is shifted, resulting in a bone deficit. Examples of such bone remodelling disorders include osteoporosis, Paget's disease, osteoarthritis, rheumatoid arthritis, achondroplasia, osteochodrytis, hyperparathyroidism, osteogenesis imperfecta, congenital hypophosphatasia, fribromatous lesions, fibrous displasia, multiple myeloma, abnormal bone turnover, osteolytic bone disease and periodontal disease. Bone remodelling disorders includes metabolic bone diseases which are characterised by disturbances in the organic matrix, bone mineralization, bone remodelling, endocrine, nutritional and other factors which regulate skeletal and mineral homeostasis. Such disorders may be hereditary or aquired and generally are systemic affecting the entire skeletal system.

Thus, in one aspect the human may have a bone remodelling disorder. Bone remodelling as used herein refers to the process whereby old bone is being removed and new bone is being formed by a continuous turnover of bone matrix and mineral that involves bone resorption by osteoclasts and bone formation by osteoblasts.

Osteoporosis is a common bone remodelling disorder characterised by a decrease in bone density of normally mineralised bone, resulting in thinning and increased porosity of bone cortices and trabeculae. The skeletal fragility caused by osteoporosis predisposes sufferers to bone pain and an increased incidence of fractures. Progressive bone loss in this condition may result in a loss of up to 50% of the initial skeletal mass.

Primary osteoporosis includes idiopathic osteoporosis which occurs in children or young adults with normal gonadal function, Type I osteoporosis, also described as post-menauposal osteoporosis, and Type II osteoporosis, senile osteoporosis, occurs mainly in those persons older than 70 years of age. Causes of secondary osteoporosis may be endocrine (e.g. glucocorticoid excess, hyperparathyroidism, hypoganodism), drug induced (e.g. corticosteroid, heparin, tobaco) and miscellanous (e.g. chronic renal failure, hepatic disease and malasorbtion syndrome osteoporosis). The phrase "at risk of developing a bone deficit"; as used herein, is intended to embrace mammals and humans having a higher than average predisposition towards developing a bone deficit. As an example, those susceptible towards osteoporosis include post-menopausal women, elderly males (e.g. those over the age of 65) and those being treated with drugs known to cause osteoporosis as a side-effect (e.g. steroid-induced osteoporosis). Certain factors are well known in the art which may be used to identify those at risk of developing a bone deficit due to bone remodelling disorders like osteoporosis. Important factors include low bone mass, family history, life style, estrogen or androgen deficiency and negative calcium balance. Post-menopausal women are particularly at risk of developing osteoporosis. Hereinafter, references to treatment of bone diseases are intended to include management and/or prophylaxis except where the context demands otherwise.

The methods of the invention may also be used to enhance bone formation in conditions where a bone deficit is caused by factors other than bone remodelling disorders. Such bone deficits include fractures, bone trauma, conditions associated with post-traumatic bone surgery, post-prosthetic joint surgery, post plastic bone surgery, post dental surgery, bone chemotherapy, post dental surgery and bone radiotherapy. Fractures include all types of microscopic and macroscopic fractures. Examples of fractures includes avulsion fracture, comminuted fracture, transverse fracture, oblique fracture, spiral fracture, segmental fracture, displaced fracture, impacted fracture, greenstick fracture, torus fracture, fatigue fracture, intraarticular fracture (epiphyseal fracture), closed fracture (simple fracture), open fracture (compound fracture) and occult fracture.

As previously mentioned, a wide variety of bone diseases may be treated in accordance with the present invention, for example all those bone diseases connected with the bone-remodelling cycle. Examples of such diseases include all forms of osteoporosis, osteomalacia, rickets and Paget's disease. Osteoporosis, especially of the post-menopausal, male and steroid-induced types, is of particular note. In addition, lanthanum compounds find use as antiresorption agents generally, as bone promotion agents and as anabolic bone agents. Such uses form another aspect of the present invention.

The present inventors have surprisingly found that lanthanum stimulates osteoblast differentiation. Osteoblast differentiation was measured in vitro cultures of bone marrow derived osteoprogenitor cells, which are capable of proliferating and differentiating into mature osteoblasts, capable of forming mineralised bone nodules. Differentation was measured by determining the specific activities of intracellular alkaline phosphatase. Low doses of lanthanum (100 ng/ml) were found to stimulate osteoblast differentiation.

The present inventors have also surprisingly found that lanthanum inhibits osteoclast differentiation in vitro, as measured by a decrease in TRAP (Tartrate-Resistant acid phosphatase) positive multinucleate cells in mouse bone marrow culture compared to control cultures. In many bone remodelling disorders, including osteoporosis, the bone deficit may be attributed to excess bone resorption by differentiated osteoclasts. The methods and compositions of the invention may be employed to inhibit osteoclast differentiation, thus inhibiting bone resorption. Some inhibition of bone resorption was found in vitro.

Low doses of lanthanum have thus been found to both enhance bone formation and stimulate osteoblast differentiation and also to inhibit osteoclast differentiation and bone resorption.

A range of lanthanum compounds may be used in the methods and compositions of the invention, preferably lanthanum (III) in a form that is bioavailable. Preferred lanthanum compounds include, for example, lanthanum salts and derivatives thereof, lanthanum resins and lanthanum absorbants. The lanthanum may if desired be in the form of a chelate. Examples of suitable lanthanum salts include lanthanum carbonate, lanthanum carbonate hydrate, lanthanum chloride.

An effective amount of lanthanum for use in the present invention is an amount of lanthanum (III)compound that will provide the desired benefit or therapeutic effect upon administration according to the prescribed regimen. Nonlimiting examples of an effective amount of lanthanum may range from about 0.01 mg/kg/day to about 100 mg/kg/day, preferably from about 0.05 mg/kg/day to about 50 mg/kg/day and more preferably from about 0.1 mg/kg/day to about 10 mg/kg/day.

The dose may also be selected to provide an effective plasma concentration of lanthanum.

Examples of an effective plasma concentration of lanthanum concentration may range from about 0.1 ng/ml to about 1000 ng/ml, preferably from about 1 ng/ml to about 500 ng/ml, more preferably from about 1 ng/ml to about 100 ng/ml.

The dose may further be selected to provide an effective level of lanthanum in and around the bone surface.

Examples of effective amounts in and around the major bone surfaces may range from 0.1 μg/g to 500 μg/g, preferably from 0.5 μg/g to 100 μg/g, more preferably from 1 μg/g to 25 μg/g.

The term "lanthanum compound" is used herein to denote any pharmacologically acceptable lanthanum compound capable of ensuring that the lanthanum is bioavailable. Preferred compounds include, for example, lanthanum salts and derivatives thereof, lanthanum resins and lanthanum absorbants. The lanthanum may if desired be in the form of a chelate. Hereinafter, the invention will be described with specific reference to certain lanthanum salts and derivatives.

The lanthanum compounds of the invention may be administered in the form of a pharmaceutical composition comprising the active ingredient in admixture or association with a pharmaceutically acceptable carrier or diluent. The active ingredient may be formulated into a composition suitable for administration by any convenient route, e.g. orally (including sublingually), topically, parenterally (including intravenous, intramuscular, intraperitoneal and subcutaneous administration) and rectally, oral administration being preferred. It should be understood, however, that the invention embraces all forms of administration which make the lanthanum systemically or locally available. Orally administrable compositions may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions may advantageously be prepared in dosage unit form. Tablets and capsules according to the invention may, if desired, contain conventional ingredients such as binding agents, for example syrup, acacia, gelatin, sorbitol, tragacanth or polyvinylpyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

Formulations for oral delivery may be formulated in a delayed release formulation such that the lanthanum is delivered to the large intestine. This will lessen the interaction of lanthanum with dietary phosphate which results in the precipitation of lanthanum phosphate, which is poorly absorbed by the gut. Delayed release formulations are well known in the art and include for example, delayed release capsules or time pills, osmotic delivery capsules etc.

Compositions for parenteral administration may be formulated using an injectable liquid carrier such as sterile pyrogen-free water, sterile peroxide-free ethyl oleate, dehydrated alcohol or propylene glycol or a dehydrated alcohol/propylene glycol mixture, and may be injected intravenously, intraperitoneally, subcutaneously or intramuscularly.

Compositions for rectal administration may be formulated using a conventional suppository base such as cocoa butter or another glyceride.

Compositions for topical administration include ointments, creams, gels, lotions, shampoos, paints, powders (including spray powders), pessaries, tampons, sprays, dips, aerosols, pour-ons and drops. The active ingredient may, for example, be formulated in a hydrophilic or hydrophobic base as appropriate.

It may be advantageous to incorporate an antioxidant, for example ascorbic acid, butylated hydroxyanisole or hydroquinone in the compositions of the invention to enhance their storage life.

Administration in this invention may consist of one or more cycles; during these cycles one or more periods of osteoclastic and osteoblastic activity will occur, as well as one or more periods when there is neither osteoclastic nor osteoblastic activity.

Alternatively, administration may be conducted in an uninterrupted regimen; such a regimen may be a long term regimen, e.g. a permanent regimen.

It will be understood that the dosages of compositions and the duration of administration according to the invention will vary depending on the requirements of the particular subject. The precise dosage regime will be determined by the attending physician or veterinary surgeon who will, inter alia, consider factors such as body weight, age and symptoms (if any). The compositions may if desired incorporate one or more further active ingredients.

During the dosing regimen, administration may be effected once or more times per day, for example once, twice, three or four times per day.

If desired, the lanthanum compound may be administered simultaneously or sequentially with other active ingredients.

These active ingredients may, for example include other medicaments or compositions capable of interacting with the bone remodelling cycle and/or which are of use in fracture repair. Such medicaments or compositions may, for example, be those of use in the treatment of osteoarthritis or osteoporosis.

Bone enhancing agents, known in the art to increase bone formation, bone density or bone mineralisation, or to prevent bone resorption may be used in the methods and pharmaceutical compositions of the invention. Suitable bone enhancing agents include natural or synthetic hormones, such as estrogens, androgens, calcitonin, prostaglandins and parathormone; growth factors, such as platelet-derived growth factor, insulin-like growth factor, transforming growth factor, epidermal growth factor, connective tissue growth factor and fibroblast growth factor; vitamins, particularly vitamin D; minerals, such as calcium, aluminum, strontium and fluoride; statin drugs, including pravastatin, fluvastatin, simvastatin, lovastatin and atorvastatin; agonsists or antagonsist of receptors on the surface of osteoblasts and osteoclasts, including parathormone receptors, estrogen receptors and prostaglandin receptors; bisphosphonate and anabolic bone agents.

FIGS. 1 to 4 show the effect of the lanthanum (III) ion on bone resorption, osteoclast differentiation, osteoblast differentiation and bone formation respectively.

The following non-limiting examples describing the effect of a lanthanum (III) ion-containing solution in vitro bone culture assays and in vivo study are illustrative of the present invention.

EXAMPLE 1

In Vitro Bone Resorption Assay

Test Substance

The test substance was lanthanum carbonate tetrahydrate (hereinafter lanthanum carbonate). 1 mg of lanthanum is equivalent to 1.9077 mg of lanthanum carbonate. Lanthanum carbonate was dissolved in 2M HCl to give a concentration of 28.6 mg/ml (i.e 15 mg/ml of lanthanum). Aliquots of this stock solution were diluted with 2M HCl to result in solutions of varying concentrations, so that addition of one microliter of these solutions into the culture medium gave the final test concentrations of 100, 500, 1000, 5000 and 15000 ng/ml of lanthanum in culture medium. These solutions/concentrations are hereinafter referred to as LA100, LA500, LA1000, LA5000 and LA15000.

Control Substances

We used control groups in each assays to show that the assays were capable of detecting the effect of inhibition (bone resorption assay and osteoclast differentiation assay) or activation (osteoblast differentiation and bone formation). The control substances used were:

Bafilomycin Al (in bone resorption assay)

17-β estradiol (in osteoblast differentiation assay and bone formation assay)

In the osteoclast differentiation assay, the control group did not contain vitamin D.

The method of osteoclast culture on bone slices was originally described by Boyde et al. (1984) and by Chambers et al. (1984). For cell culture, we used a method slightly modified from the original methods (Lakkakorpi et al. 1989, Lakkakorpi and Väänänen, 1991). The rate of bone resorption in the cultures was originally determined by counting the number of resorption pits on each bone or dentine slice using a microscope with phase contrast objectives (Sundquist et al. 1990). Later, the pits were visualized using Wheat Germ Agglutinin lectin that specifically binds to the resorbed area in bone (Selander et al. 1994), making it possible to quantify the total resorbed area using a microscope and computer-assisted image analysis system (Laitala and Väänänen 1994, Hentunen et al. 1995). We used a commercially available method (CrossLaps for cultures, Osteometer Biotech, Herlev, Denmark) to detect the amount of collagen cross-links released into the culture medium as an index of the bone resorption rate (Bagger et al., 1999).

The study protocol uses a method where osteoclasts are cultured on bone slices and allowed to resorb bone. The system is ideal for determining the effect of drug candidates on the bone resorbing activity of osteoclasts. Drug candidates are added into the cell cultures at the beginning of the culture period, and the osteoclasts allowed to resorb bone for 3 days. The amount of bone resorbed during the culture period is determined and compared to the amount of bone resorbed in control cultures (those cultured in the absence of drug candidates). If the drug candidate inhibits the function of osteoclasts, the amount of bone resorbed in these cultures is significantly lower than in the control cultures.

Procedure:

Transverse 0.1 mm thick slices of cortical bone were cut from the diaphysis of fresh bovine femurs (Atria Slaughterhouse, Oulu, Finland) using a low-speed diamond saw, cleaned by ultrasonication in multiple changes of sterile distilled water, and stored at 4° C. before use. Long bones were removed from 1-day-old rat pups killed by decapitation. The bones were dissected free of adherent soft tissues, and the endosteal surfaces were curetted with a scalpel blade into the osteoclast culture medium (Dulbecco s Modified Eagle s Medium (DMIEM), (Gibco BRL, Paisley, UK)) supplemented with 100 IU/ml penicillin, 100 μg/ml streptomycin (Penicillin/Streptomycin solution, Gibco BRL, Paisley, UK), 20 mM HEPES buffer (Gibco BRL, Paisley, UK) and 10% heat-inactivated fetal calf serum, pH 6.9 (Gibco BRL, Paisley, UK). The resulting suspension of dispersed cells and bone fragments was agitated using a plastic pipette. Larger fragments were allowed to sediment for a few seconds and the supernatant was seeded onto the bone slices pre-wetted in the medium. After a settling period of 30 minutes at 37° C., the bone slices were washed by dipping in fresh medium, and then transferred to wells in 24-well culture dishes containing osteoclast culture medium. The bone slices were incubated in a humidified atmosphere of 95% air and 5% carbon dioxide at 37° C. for 72 hours.

After the culture period, the amount of bone resorption was determined by measuring the amount of collagen cross-links released into the culture medium using a commercial kit (CrossLaps for cultures, Osteometer Biotech) according to the manufacturer s instructions. The number of osteoclasts in each culture was determined by microscopic counting of the amount of TRAP-positive multinuclear cells, and the results are given as the number of collagen cross-links released per one osteoclast.

In this study, the effect of the lanthanum (III) ion on the bone resorbing activity of osteoclasts was tested.

The following sample groups were included:

Baseline (including vehicle)

Control (Baseline+10 nM bafilomycin Al)

Baseline+100 ng/ml lanthanum

Baseline+500 ng/ml lanthanum

Baseline+1000 ng/ml lanthanum

Baseline+5000 ng/ml lanthanum

Baseline+15000 ng/ml lanthanum

Six replicates were included in each group, and the test was performed twice. Bafilomycin Al, a highly potent inhibitor of osteoclast V-ATPase proton pump, was used as a control to show the ability of the test system to detect inhibition of bone resorption.

Tables of Results:

In the bone resorption assay, the amount of medium CrossLaps (nM) released into the culture medium was determined and the number of osteoclasts in the corresponding cultures calculated. The medium CrossLaps amounts were divided with the osteoclast numbers in the corresponding cultures, and the results are given on Table 1 as relative medium CrossLaps amounts per osteoclasts. The relative values were obtained by dividing each individual value with the mean value of the baseline group.

TABLE 1

Relative medium CrossLaps amounts per osteoclast in the first bone resorption assay

| Group | 1 | 2 | 3 | 4 | 5 | 6 | Mean ± SD |
|---|---|---|---|---|---|---|---|
| Baseline | 0.98 | 0.82 | 1.01 | 1.65 | 0.74 | 0.81 | 1.00 ± 0.34 |
| Control | 0.00 | 0.00 | 0.00 | 0.19 | 0.27 | 0.14 | 0.10 ± 0.11(***) |
| LA 100 | 0.57 | 0.56 | 1.13 | 0.78 | 0.71 | 0.71 | |
| LA 500 | 1.04 | 0.58 | 1.38 | 0.75 | 0.88 | 0.63 | 0.74 ± 0.21 |
| LA 1000 | 1.14 | 1.09 | 0.89 | 1.76 | 1.07 | 1.11 | 0.88 ± 0.30 |
| LA 5000 | 1.39 | 0.78 | 2.70 | 1.18 | 0.76 | 1.21 | 1.18 ± 0.30 |
| LA 15000 | 0.57 | 0.58 | 0.57 | 0.96 | 2.53 | 1.11 | 1.34 ± 0.71 |
| | | | | | | | 1.05 ± 0.76 |

TABLE 2

Relative medium CrossLaps amounts per osteoclasts in the second bone resorption assay

| Group | 1 | 2 | 3 | 4 | 5 | 6 | Mean ± SD |
|---|---|---|---|---|---|---|---|
| Baseline | 0.75 | 1.33 | 0.88 | 1.98 | 0.53 | 0.53 | 1.00 ± 0.56 |
| Control | 0.00 | 0.00 | 0.00 | 0.00 | 0.00 | 0.00 | 0.00 ± 0.00(***) |
| LA 100 | 0.38 | 0.75 | 0.78 | 0.94 | 0.67 | 0.96 | |
| LA 500 | 0.50 | 2.14 | 0.50 | 1.03 | 0.47 | 0.63 | 0.74 ± 0.21 |
| LA 1000 | 0.70 | 0.59 | 1.69 | 1.40 | 1.68 | 0.73 | 0.88 ± 0.65 |
| LA 5000 | 0.48 | 1.18 | 0.77 | 0.98 | 1.99 | 1.81 | 1.13 ± 0.51 |
| LA 15000 | 0.29 | 1.08 | 0.62 | 0.87 | 0.47 | 0.45 | 1.20 ± 0.59 |
| | | | | | | | 0.63 ± 0.29 |

All data shown on tables 1 and 2 were combined and analyzed.

Figure 1:
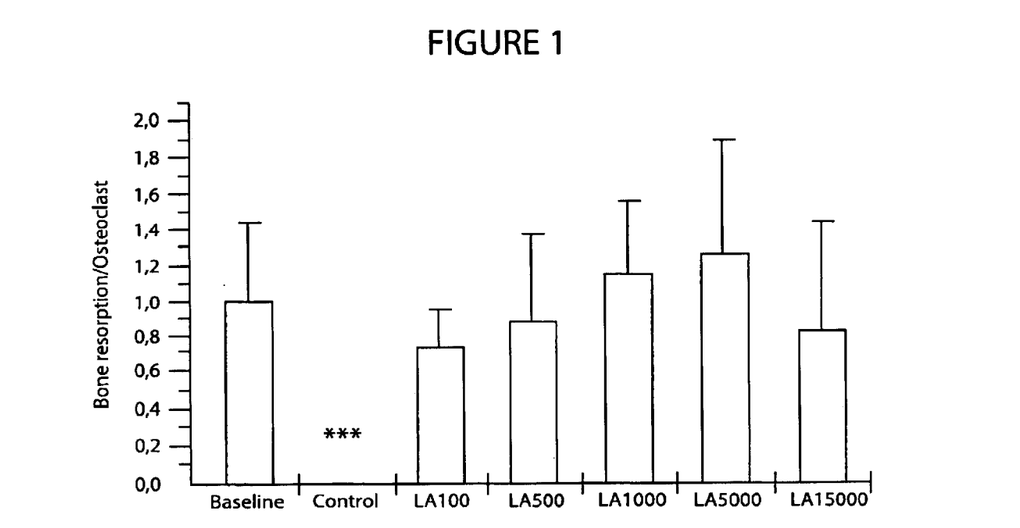
FIG. 1 is a bar graph showing the combined results of the effect of LA on bone resoption, where the bars represent the relative medium CrossLaps amounts per osteoclast ±SD at different lanthanum concentrations.
Figure 2:
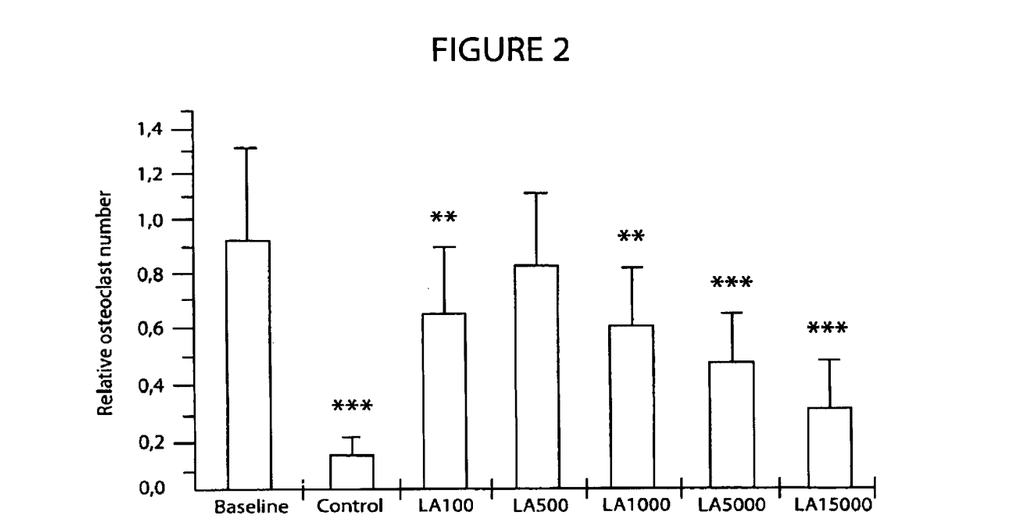
FIG. 2 is a bar graph showing the combined results of the effect of LA on osteoclast differentiation, where the bars represent the relative TRAP 5b activities ±SD at different lanthanum concentrations.
Figure 3:
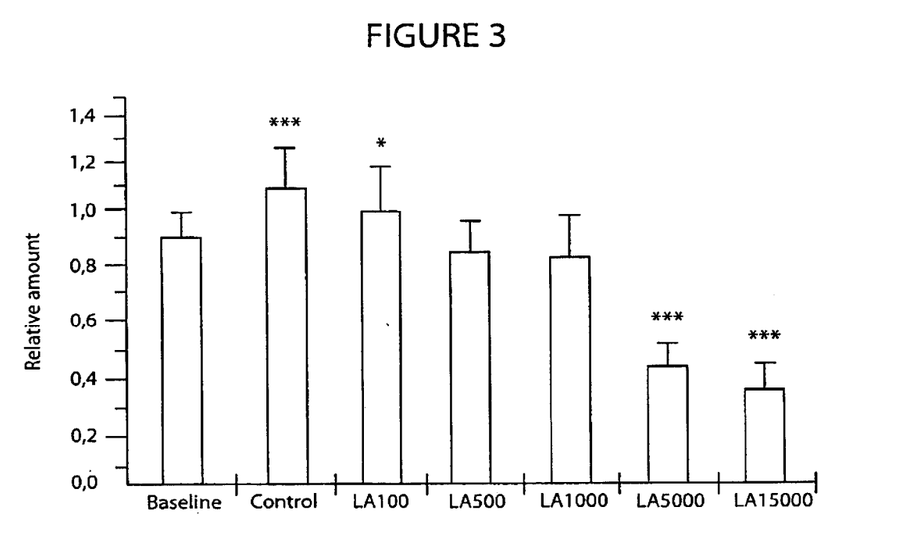
FIG. 3 is a bar graph showing the combined results of the effect of LA on osteoblast differentiation, where the bars represent relative specific activities of cellular alkaline phosphatase ±SD at different lanthanum concentrations.
Figure 4:
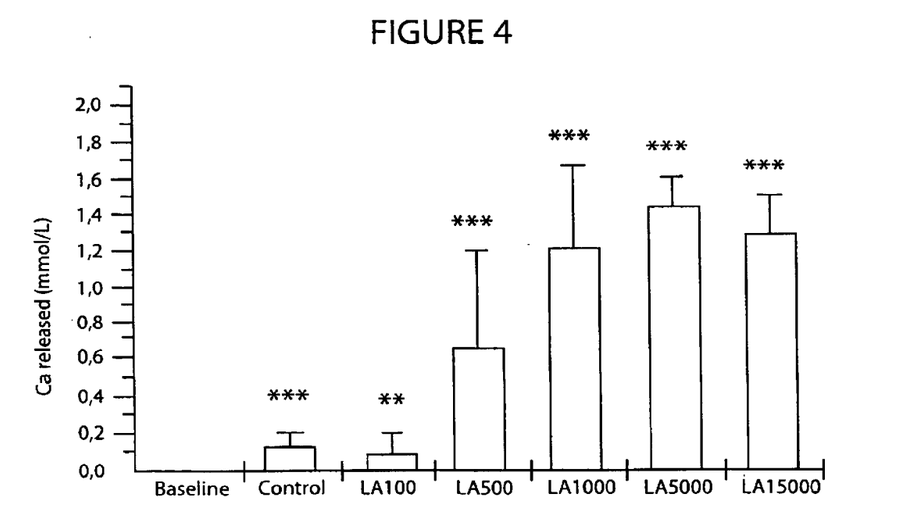
FIG. 4 is a bar graph showing the combined results of the effect of LA on bone formation activity of mature osteoblasts, where the bars represent the amount of calcium released (mmol/L) from the bone nodules after HCl extraction. ±SD at different lanthanum concentrations.

The combined results are shown on table 3 and FIG. 1.

TABLE 3

Combined results of the effect of LA 100 - LA 15000 on bone resorption

| Group | number | Mean ± SD |
|---|---|---|
| Baseline | 12 | 1.00 ± 0.44 |
| Control | 12 | 0.00 ± 0.00 (***) |
| LA 100 | 12 | 0.74 ± 0.20 |
| LA 500 | 12 | 0.88 ± 0.48 |
| LA 1000 | 12 | 1.15 ± 0.40 |
| LA 5000 | 12 | 1.27 ± 0.63 |
| LA 15000 | 12 | 0.84 ± 0.59 |

Results

In the bone resorption assay, there was no significant effect of the lanthanum (III) ion on either the amount of CrossLaps released into the culture medium or on the osteoclast number. The control substance, bafilomycin Al, completely inhibited bone resorption. As shown on table 3 and FIG. 4, the lanthanum (III) ion has no statistically significant effects on the bone resorbing activity of individual mature osteoclasts at any of the concentrations tested. However, the dose-dependent inhibition of bone resorption with the lower concentrations (LA 100 and LA 500) should be noticed. The slight decrease seen with LA 15000 may be due to slight toxic effects of this high concentration.

References:

Bagger Y Z, Foged N T, Andersen L, Lou H, Qvist P (1999) CrossLaps for culture: An improved enzyme-linked immunosorbent assay (ELISA) for measuring bone resorption in vitro. J Bone Miner Res 14, Suppl. 1, S370.

Boyde A, Ali N N, Jones S J (1984) Resorption of dentine by isolated osteoclasts in vitro. Br Dent J 156: 216–220.

Chambers T J, Revell P A, Fuller K, Athanasou N A (1984) Resorption of bone by isolated rabbit osteociasts. J Cell Sci 66: 383–399.

Hentunen T A, Lakkakorpi P T, Tuukkanen J, Lehenkari P P, Sampath T K, Väänänen B K (1995) Effects of recombinant human osteogenic protein-1 on the differentiation of osteoclast-like cells and bone resorption. Biochem Biophys Res Commun 209: 433–443.

Laitala T, Väänänen H K (1994) Inhibition of bone resorption in vitro by antisense RNA and DNA molecules targeted against carbonic anhydrase II or two subunits of vacuolar H+-ATPase. J Clin Invest 93: 2311–2318.

Lakkakorpi F, Tuukkanan I, Hentunen T, Järvelin K, Väänänen H K (1989) Organization of osteoclast microfilaments during the attachment to bone surface in vitro. I Bone Miner Res 4:8 17–825.

Lakkakorpi P T, Väänänen H K (1991) Kinetics of the osteoclast cytoskeleton during the resorption cycle in vitro. J Bone Miner Res 6: 817.826.

Selander K, Lehenkari P, Väänänen H K (1994) The effects of bisphosphonates on the resorption cycle of isolated osteoclasts. Calcif Tissue Int 55: 368–375.

Sundquist K, Lakkakorpi P, Wallmark B, Väänänen H K (1990) Inhibition of osteoclast proton transport by bafilomycin $A_1$ abolishes bone resorption. Biochem Biophys Res Commun 168: 309–313.

EXAMPLE 2

In Vitro Osteoclast Differentiation Assay

A method known as mouse bone marrow culture system is the one most widely used to study osteoclast differentiation. Originally, this method was developed by Takahashi et al. (1988a). Osteoclast precursors in mouse bone marrow can be induced to form multinucleated osteoclast-like cells (MNC) in the presence of either an active metabolite of vitamin $D_3$ ($1,25(OH)_2D_3$) or parathyroid hormone (PTH). MNC formed in mouse bone marrow cultures have been demonstrated to possess several features characteristic of osteoclasts. They form pits on bone or dentine slices (Takahashi et al. 1988a, Hattersley and Chambers 1989, Shinar et al. 1990); they express high levels of tartrate-resistant acid phosphatase (TRAP) and calcitonin receptors (Takahashi et al. 1988b, Shinar et al. 1990); and they respond to calcitonin (Takahashi et al. 1988a) and prostaglandin $E_2$ (Collins and Chambers 1992). Thus, the method is an ideal one with which to study both stimulators and inhibitors of osteoclast differentiation.

In the original culture system, the osteoclast formation was determined after an 8-day culture. In bone marrow, both non-adherent osteoclast precursors and stromal cells are present, the latter of which are needed to support osteoclast formation. The number of osteoclasts formed is generally determined by counting the number of TRAP-positive MNC containing at least three nuclei (Takahashi et al. 1988a). In the negative control, where 1,25(OH)$_2$D$_3$ is not added, TRAP-positive MNC are not formed.

We have modified the original assay so that we culture 1×10$^6$ mouse marrow cells/ml for 6 days. With this modification, the number of TRAP-positive MNC/culture has been shown to be approximately 150 (Choi et al. 1998, Hentunen et al. 1998). Instead of counting of the number of differentiated osteoclasts formed, we measured the amount of TRAP liberated from osteoclasts into the culture medium using a fast, simple TRAP immunoassay (Halleen et al. 1999) presentation in the Annual Meeting of the American Society for Bone and Mineral Research, Sep. 30–Oct. 4, 1999, in St. Louis, Mo., USA. Our results show that the amount of TRAP released into the culture medium correlates significantly (r=0.94, p<0.0001, n=120) with the amount of osteoclasts formed.

Procedure:

8–10-week old mice were killed with CO$_2$. Tibia and femora were dissected free from adhering soft tissues. The bone ends were cut off with a scalpel and the marrow was flushed with α-Minimal Essential Medium (α-MEM, Gibco BRL, Paisley, UK) supplemented with 100 IU/ml penicillin and 100 μg/ml streptomycin. A 10 ml syringe with a 27 gauge needle was used for flushing. Cells were centrifuged at 600×G for 10 minutes and the cell pellet was resuspended in -MEM containing 10% fetal calf serum. Cells were allowed to attach to plastic for 2 h at 37° C. in a 5% CO$_2$ incubator to allow removal of monocytes and macrophages. Nonadherent cells were duly removed, and the attached bone marrow cells were cultured in 24-well plates (1×10$^6$ cells/well=1 ml) for 6 days. Half of the media were changed at day 3 and the treatments replaced. At the end of the culture, the plates were fixed with 2% paraformaldehyde in PBS for 20 minutes. Osteoclast formation was determined by measuring TRAP activity from the culture media using the novel TRAP immunoassay (vide infra), where we use a polyclonal TRAP antiserum prepared in rabbits against purified human bone TRAP. The TRAP antibody was bound to anti-rabbit IgG coated microtiter wells (Gibco BRL, Paisley, UK), and medium TRAP was then bound to the antibody. The activity of bound TRAP was measured in sodium acetate buffer using pNPP as substrate.

In this study, the effect of the lanthanum (III) ion on osteoclast differentiation in the presence of 1,25-dihydroxyvitamin D3 was tested. The following sample groups were included:

Baseline (including vehicle)
Control (Baseline without 1,25-dihydroxyvitamin D3)
Baseline+100 ng/ml lanthanum
Baseline+500 ng/ml lanthanum
Baseline+1000 ng/ml lanthanum
Baseline+5000 ng/ml lanthanum
Baseline+15000 ng/ml lanthanum Six replicates were included in each group, and the test was performed twice. Baseline without 1,25-dihydroxyvitamin D3 was used as a control to show the test system allows inhibition of osteoclast differentiation to be detected. As the results of LA100 did not give statistically the same result (significantly different or not compared with the baseline) in both of the two tests, we performed the test with LA100 one additional time.

Tables of Results:

In the osteoclast differentiation assay, the amount of TRAP 5b activity released into the culture medium was determined as an index of osteoclast number. The results are shown as relative TRAP 5b activities obtained by dividing each individual TRAP 5b activity with the mean TRAP 5b activity of the baseline group.

TABLE 4

Relative TRAP 5b activities in the first osteoclast differentiation assay

| Group | 1 | 2 | 3 | 4 | 5 | 6 | Mean ± SD |
|---|---|---|---|---|---|---|---|
| Baseline | 1.32 | 0.72 | 0.43 | 0.45 | 1.89 | 1.18 | 1.00 ± 0.57 |
| Control | 0.16 | 0.17 | 0.18 | 0.11 | 0.11 | 0.20 | 0.16 ± 0.04(**) |
| LA 100 | 0.81 | 0.96 | 0.43 | 1.39 | 0.98 | 0.65 | |
| LA 500 | 0.73 | 0.55 | 0.48 | 0.87 | 0.58 | 1.05 | 0.87 ± 0.33 |
| LA 1000 | 0.58 | 0.82 | 0.35 | 0.40 | 0.98 | 0.45 | 0.71 ± 0.22 |
| LA 5000 | 0.44 | 0.40 | 0.41 | 0.36 | 0.51 | 0.52 | 0.60 ± 0.25 |
| LA 15000 | 0.14 | 0.26 | 0.21 | 0.34 | 0.31 | 0.88 | 0.44 ± 0.06(*) |
| | | | | | | | 0.36 ± 0.27(*) |

TABLE 5

Relative TRAP 5b activities in the second osteoclast differentiation assay

| Group | 1 | 2 | 3 | 4 | 5 | 6 | Mean ± SD |
|---|---|---|---|---|---|---|---|
| Baseline | 1.27 | 1.37 | 0.98 | 0.92 | 0.74 | 0.71 | 1.00 ± 0.27 |
| Control | 0.17 | 0.34 | 0.14 | 0.10 | 0.11 | 0.06 | 0.15 ± 0.10(***) |
| LA 100 | 0.64 | 0.66 | 0.62 | 0.36 | 0.33 | 0.62 | |
| LA 500 | 1.16 | 1.30 | 0.85 | 1.33 | 0.76 | 1.01 | 0.54 ± 0.15(**) |
| LA 1000 | 0.70 | 0.78 | 0.34 | 0.65 | 0.69 | 1.00 | |
| LA 5000 | 0.94 | 0.46 | 0.21 | 0.72 | 0.68 | 0.33 | 1.07 ± 0.24 |
| LA 15000 | 0.22 | 0.31 | 0.35 | 0.25 | 0.15 | 0.20 | 0.69 ± 0.21 |
| | | | | | | | 0.56 ± 0.27(*) |
| | | | | | | | 0.25 ± 0.07(***) |

The assay with LA 100 was repeated one more time, because the results were significantly different from baseline in the second assay, and not significantly different in the first assay.

TABLE 6

Relative TRAP 5b activities in the third osteoclast differentiation assay with LA 100.

| Group | 1 | 2 | 3 | 4 | 5 | 6 | Mean ± SD |
|---|---|---|---|---|---|---|---|
| Baseline | 1.25 | 1.20 | 0.76 | 0.93 | 1.07 | 0.81 | 1.00 ± 0.20 |
| Control | 0.08 | 0.07 | 0.20 | 0.10 | 0.25 | 0.13 | 0.14 ± 0.07(***) |
| LA 100 | 0.71 | 0.96 | 0.42 | 0.47 | 0.87 | 0.69 | |
| | | | | | | | 0.69 ± 0.21(*) |

All data shown on tables 4–6 were combined and analyzed. The combined results are shown on table 7 and FIG. 2.

TABLE 7

Combined results of the effect of LA 100 - LA1 5000 on osteoclast differentiation

| Group | number | Mean ± SD |
|---|---|---|
| Baseline | 18 | 1.00 ± 0.36 |
| Control | 18 | 0.15 ± 0.07 (***) |
| LA 100 | 18 | 0.70 ± 0.27 (**) |
| LA 500 | 12 | 0.89 ± 0.29 |
| LA 1000 | 12 | 0.65 ± 0.23 (**) |
| LA 5000 | 12 | 0.50 ± 0.20 (***) |
| LA 15000 | 12 | 0.30 ± 0.19 (***) |

Results:

In the osteoclast differentiation assay, a clear dose-dependent inhibition was observed with LA 500–LA 15000 that was statistically significant from LA 1000 to LA 15000. A statistically significant inhibition was also observed with LA 100. In the control group where vitamin D was omitted, osteoclast differentiation was significantly lower than in the baseline group.

References

Halleen N, Alatalo S, Hentunen T A, Väänänen H K (1999) A novel TRAP 5b immunoassay for osteoclast cultures. J Bone Miner Res 14, Suppl. 1, S244.

Choi S J, Devlin R D, Menaa C, Chung H, Roodman G D, Reddy S V (1998) Cloning and identification of human Sca as a novel inhibitor of osteoclast formation and bone resorption. J Clin Invest 102: 1360–1368.

Collins D A, Chambers T J (1992) Prostaglandin $E_2$ promotes osteoclast formation in murine hematopoietic cultures through an action on hematopotetic cells. J Bone Miner Res 7: 555–561.

Hattersley G, Chambers T J (1989) Generation of osteoclastic function in mouse bone marrow cultures: multinuclearity and tartrate-resistant acid phosphatase are unreliable markers for ostcoclastic differentiation. Endocrinology 124: 1689–25 1696.

Hentunen T A, Reddy S V. Boyce B F, Dovlin R, Park H-R, Chimg H, Selander K S, Dallas M, Kurihara N, Galson O L, Goldring S R, Koop, B A Windle J J, Roodman G D (1998) Immortalization of osteoclast precursors by targeting bcl-$X_L$ and simian virus 40 large T antigen to the osteoclast lineage in transgenic mice. J Clin Invest 102: 88–97.

Shinar D M, Sato M, Rodan G A (1990) The effect of hemopoietic growth factors on the generation of osteoclast-like cells in mouse bone marrow cultures. Endocrinology 126: 1728–1735.

Takahashi N, Yamana H, Yoshiki S, Roodman G D, Mundy G R, Jones S J, Boyde A, Suda T (1988a) Osteoclast-Like cell formation and its regulation by osteotropic hormones in mouse bone marrow cultures. Endocrinology 122:1373–1382.

Takahashi N. Akatsu T, Sasaki T, Nicholson G C, Moseley J M, Martin T J, Suda T (1988b) Induction of calcitonin receptors by 1,25-dihydroxyvitamin $D_3$ in osteoclast-like multinucleated cells formed from mouse bone marrow cells. Endocrinology 123: 1504–1510.

EXAMPLE 3

In Vitro Osteoblast Differentiation Assay

Osteoblasts are bone-forming cells which arise from mesenchymal stem cells. During the development of osteoblasts, three distinct periods have been identified and defined: 1) cell proliferation and secretion of extracellular matrix (ECM); 2) ECM maturation; and 3) ECM mineralization. During these periods, a sequential expression of osteoblast phenotype markers has been characterized. Alkaline phosphatase is associated with the bone cell phenotype and is actively expressed during the maturation of the osteoblast. With the onset of mineralization, large amounts of calcium are deposited into the mature organic matrix to form bone-like nodules. By following these markers, we are able to study all the stages of osteoblast differentiation in this culture system.

Several methods have been devised to study osteoblasts. The first of these involves isolation of cells from calvaria with the osteoblastic phenotype. However, these cells only represent the mature stage of osteoblasts, because only a small fraction of the calvarial cells are osteoblast precursors (Bellows and Aubin 1989, Bellows et al. 1994). Osteoblastic cell lines are convenient in use, but they may not behave as primary osteoblasts (Mundy 1995). It is conceivable that osteoblast precursors are present in bone marrow (Friedenstein 1976, Owen 1988), and bone marrow stromal cells have long been recognized as the source of osteoprogenitor cells.

We have established a culture model in which mouse bone marrow derived osteoprogenitor cells first proliferate and then differentiate to osteoblasts capable of forming mineralized bone nodules (Qu et al. 1998, Qu et al. 1999). We confirmed this by following the expression of several markers of the osteoblastic phenotype and by studying the morphology of cultures at light and electron microscopic level. Synthesis of fibrillar extracellular matrix with late deposition of calcium confirmed the differentiation and maturation of osteoblasts. Thus, this culture system fulfills requirements of an in vitro model useful for studying differentiation of osteoprogenitor cells into bone synthesizing osteoblasts.

Procedure:

Bone marrow cells were obtained from the femurs of 10-week old female NMRI mice. Animals were killed by cervical dislocation. Both femora were removed and the soft tissues were detached aseptically. Metaphyses from both ends were cut off and bone marrow cells were collected by flushing the diaphysis with culture medium: phenol red-free-α-modified essential medium (α-MEM (Gibco BRL, Paisley, UK)). A suspension of bone marrow cells was obtained by repeated aspiration of the cell preparation through a 22 gauge needle, and nucleated cells were counted with a hemocytometer. Cells were plated at $10^6$ cells/cm$^2$ in T-75 tissue culture flasks in phenol red-free α-MEM supplemented with 10% FCS, $10^{-8}$ M dexamethasone, 50 μg/ml ascorbic acid, $10^{-2}$ M sodium β-glycerophosphate, 100 IU/ml penicillin and 100 μg/ml streptomycin. The cells were cultured for 6 days and half of the media replaced after 3 days. On day 6, subcultures were prepared. Cells were washed with warm PBS and adherent cells were detached using trypsin-EDTA. Trypsinized cells were passed through a syringe with a 22 gauge needle to make a single-cell suspension, counted and plated in 24-well plates at a density of $5 \times 10^3$ cells/ml. These osteoprogenitor cells were stimulated to differentiate towards mature osteoblasts by culturing them in the presence of $10^{-10}$ M estrogen (17β-estradiol) for 8 days. The test substances were added at the beginning of the secondary culture without estrogen, and every time when the medium was changed.

The number of osteoblasts formed was determined by measuring cellular alkaline phosphatase (ALP) activity in the culture. Cells were disrupted by washing the cell layers twice with PBS, extracting into 200 μl 0.1% Triton X-100 buffer at pH 7.6 (Sigma, St. Louis, Mo., USA), and overnight freezing. ALP activity was determined colorimetrically using p-nitrophenylphosphate as substrate at pH 9.7 and determining the optical density at 405 nm. In parallel, protein contents of the wells were determined by the BIO-RAD protein assay, and the specific ALP activity is expressed as units/mg protein.

In this study, the effect of the lanthanum (III) ion on osteoblast differentiation was tested. The following sample groups were included:

Baseline (+vehicle)
Control (Baseline+$10^{-10}$ M 17-estradiol)
Baseline+100 ng/ml lanthanum Baseline+500 ng/ml lanthanum
Baseline+1000 ng/ml lanthanum
Baseline+5000 ng/ml lanthanum
Baseline+15000 ng/ml lanthanum Tables of Results:

Osteoblast differentiation was determined by measuring cellular alkaline phosphatase (ALP) activities and total protein amounts from cell lysates. The ALP activities were divided with the corresponding protein amounts to obtain specific activities of ALP. The results are shown as relative specific activities obtained by dividing each individual value with the mean value of the baseline group.

TABLE 8

Relative specific activities of intracellular alkaline phosphatase in the preliminary osteoblast differentiation assay

| Group | 1 | 2 | 3 | 4 | Mean ± SD |
|---|---|---|---|---|---|
| Baseline | 0.94 | 1.10 | 0.94 | 1.02 | 1.00 ± 0.07 |
| Control | 1.10 | 1.32 | 1.31 | 1.29 | 1.26 ± 0.10(**) |
| LA 100 | 0.98 | 1.29 | 1.19 | 1.12 | 1.15 ± 0.13 |
| LA 500 | 0.96 | 0.98 | 0.99 | 1.11 | 1.01 ± 0.07 |
| LA 1000 | 0.69 | 1.13 | 0.92 | 1.01 | 0.94 ± 0.19 |
| LA 5000 | 0.42 | 0.46 | 0.50 | 0.48 | 0.47 ± 0.03(***) |
| LA 15000 | 0.51 | 0.49 | 0.47 | 0.54 | 0.50 ± 0.03(***) |

TABLE 9

Relative specific activities of intracellular alkaline phosphatase in the first osteoblast differentiation assay

| Group | 1 | 2 | 3 | 4 | 5 | 6 | 7 | 8 | Mean ± SD |
|---|---|---|---|---|---|---|---|---|---|
| Baseline | 0.97 | 0.94 | 1.12 | 0.98 | 0.97 | 1.06 | 0.99 | 0.96 | 1.00 ± 0.06 |
| Control | | | 1.24 | 1.03 | 1.19 | 1.06 | | 1.14 | 1.10 ± 0.08(**) |
| | | | 1.20 | 0.94 | 0.95 | 1.04 | | 1.00 | 0.98 |
| | | | | 3 | 0.95 | 0.96 | | 3 | 0.62 1.05 ± 0.17 |
| LA 100 | 1.0 | 0.9 | 1.3 | 0.7 | 1.01 | 0.78 | 1.1 | 0.81 | 0.90 ± 0.14 |
| LA 500 | 1.8 | 1.7 | | 0.54 | 0.59 | 3 | 0.55 | 0.94 ± 0.14 |
| LA 1000 | 1.25 | 1.03 | 1.28 | 0.39 | 0.35 | 0.82 | 0.43 | 0.53 ± 0.06(***) |
| LA 5000 | 0.83 | 1.12 | 1.06 | 0.7 | | | 0.93 | 0.40 ± 0.07(***) |
| LA 15000 | 1.0 | 0.4 | 0.4 | 0.6 | | | 0.4 | |
| | 1.8 | 7 | 3 | | | | 4 | |
| | 0.5 | 0.4 | 0.5 | 0.3 | | | 0.3 | |
| | 4 | 2 | 3 | 6 | | | 0 | |
| | 0.4 | | | | | | | |
| | 0 | | | | | | | |

TABLE 10

Relative specific activities or intracellular alkaline phosphatase in the second osteoblast differentiation assay

| Group | 1 | 2 | 3 | 4 | 5 | 6 | Mean ± SD |
|---|---|---|---|---|---|---|---|
| Baseline | 0.99 | 0.83 | 1.25 | 1.01 | 0.88 | 1.04 | 1.00 ± 0.15 |
| Control | 1.00 | 1.18 | 1.53 | 1.52 | 1.03 | 1.38 | 1.27 ± 0.24(*) |
| LA 100 | 0.91 | 0.94 | 1.34 | 1.20 | 1.00 | 1.43 | 1.14 ± 0.22 |
| LA 500 | 0.88 | 0.89 | 1.10 | 1.09 | 0.75 | 0.90 | 0.93 ± 0.14 |
| LA 1000 | 0.73 | 0.71 | 1.19 | 0.81 | 0.72 | 1.09 | 0.88 ± 0.21 |
| LA 5000 | 0.31 | 0.51 | 0.51 | 0.49 | 0.28 | 0.40 | 0.41 ± 0.10(***) |
| LA 15000 | 0.27 | 0.13 | 0.33 | 0.32 | 0.29 | 0.31 | 0.28 ± 0.07(***) |

All data shown on tables 8–10 were combined and analyzed. The combined results are shown on table 11 and FIG. 3.

TABLE 11

Combined results of the effect of LA100-LA15000 on osteoblast differentiation

| Group | number | Mean ± SD |
|---|---|---|
| Baseline | 18 | 1.00 ± 0.09 |
| Control | 18 | 1.19 ± 0.17 (***) |
| LA 100 | 18 | 1.10 ± 0.18 (*) |
| LA 500 | 18 | 0.94 ± 0.13 |
| LA 1000 | 18 | 0.92 ± 0.17 |
| LA 5000 | 18 | 0.48 ± 0.09 (***) |
| LA 15000 | 18 | 0.38 ± 0.11 (***) |

Results:

The lanthanum (III) ion showed a clear dose-dependent response in the osteoblast differentiation assay. The highest test concentrations (LA 5000 and LA 15000) inhibited, and the lowest test concentration (LA 100) activated osteoblast differentiation significantly. No significant response was observed with LA 500 and LA 1000. The control substance, 17-estradiol, activated osteoblast differentiation significantly.

References

Bellows C G, Aubin J E (1989) Determination of the number of osteoprogenitors in isolated fetal rat calvarial cells in vitro. Develop Biol 113:8–13.

Bellows C G, Wang Y H. Heersche J N, Aubin J E (1994) 1,25-dihydroxyvitamin $D_3$ stimulates adipocytic differentiation in cultures of fetal rat calvarial cells: comparison with the effects of dexamethasone. Endocrinology 134:2221.2229.

Friedenstein A J (1976) Precursor cells of mechanocytes. Int Rev Cytol 47: 327–355.

Mundy R G (1995) Osteoblests, bone formation and mineralization. In: Bone remodelling and its disorders. Martin Dunitz Ltd pp. 29–30.

Owen M. Friendenstein A J (1988) Stromal stem cells: Marrow-derived osteogenic precursors. Ciba Found Symp 136:42–60.

Qu Q, Perälä-Heape M, Kapanen A, Dahllund J, Salo J, Väänanen, H K, Härkönen, P (1998) Estrogen enhances differentiation of osteoblasts in mouse bone marrow culture. Bone 22:201.209.

Qu Q, Härkönen P L, Väänänen H K (1999) Comparative effects of estrogen and antiestrogens on differentiation of osteoblasts in mouse bone marrow culture. J Cell Biochem 73: 500–507.

EXAMPLE 4

In Vitro Bone Formation Assay

The activity of mature osteoblasts can be determined by quantifying their ability to form mineralized bone matrix. This is done by demineralizing the formed bone matrix, and determining the amount of calcium released. Thus, this culture system fulfills requirements of an in vitro model useful for studying the bone formation activity of mature osteoblasts.

Procedure:

The mature osteoblasts obtained during the 8-day secondary culture in the absence of estrogen and any test substances described above were allowed to form bone nodules by culturing them for 7 additional days. At the end of the culture, the amount of calcium deposited during the culture period was determined, and the amount of bone formation (calcium deposition) calculated.

In order to quantify the amount of calcium deposited, the cell cultures were washed three times with $Ca^{2+}$- and $Mg^{2+}$-free PBS and incubated overnight at room temperature in 0.6M HCl. Extracts of 50 µl were complexed with 1 ml determined o-cresol-phthalein-complexon. The colorimetric reaction was determined at 570 nm in a spectrophotometer. Absolute calcium concentrations were determined by comparison with a calibrated standard provided by the vendor.

In this study, the effect of lanthanum carbonate on bone formation was tested. The following sample groups were included:

Baseline (including vehicle)
Control (Baseline+$10^{-10}$M 17β-estradiol)
Baseline+100 ng/ml lanthanum
Baseline+500 ng/ml lanthanum
Baseline+1000 ng/ml lanthanum
Baseline+5000 ng/ml lanthanum
Baseline+15000 ng/ml lanthanum Tables of Results:

The amount of bone formation was determined by measuring the amount of calcium deposited into bone nodules formed by mature osteoblasts. The results are shown as the amount of calcium released (mmol/L) from the bone nodules after HCl extraction. The baseline values are too low to show the results using relative amounts as was done in the other assays.

TABLE 12

Calcium deposition (mmol/L) in the preliminary bone formation assay

| Group | 1 | 2 | 3 | 4 | Mean ± SD |
|-------|------|------|------|------|-----------|
| Baseline | 0 | 0 | 0 | 0 | 0.00 ± 0.00 |
| Control | 0.04 | 0 | 0 | 0.04 | 0.02 ± 0.02 |
| LA 100 | 0 | 0 | 0 | 0 | 0.00 ± 0.00 |
| LA 500 | 0 | 0 | 0 | 0.09 | 0.02 ± 0.05 |
| LA 1000 | 0.10 | 0 | 0.11 | 0.05 | 0.07 ± 0.05 (*) |
| LA 5000 | 0.59 | 1.64 | 0.39 | 1.62 | 1.06 ± 0.66 (***) |
| LA 15000 | 1.48 | 0.16 | 0.50 | 1.41 | 0.89 ± 0.66 (***) |

TABLE 13

Calcium deposition (mmol/L) in the first bone formation assay

| Group | 1 | 2 | 3 | 4 | 5 | 6 | Mean ± SD |
|-------|------|------|------|------|------|------|-----------|
| Baseline | 0 | 0 | 0 | 0.02 | 0.02 | 0 | 0.01 ± 0.01 |
| Control | 0.15 | 0.21 | 0.14 | 0.10 | 0.15 | 0.16 | 0.15 ± 0.04 (***) |
| LA 100 | 0.04 | 0.17 | 0.01 | 0.27 | 0 | 0.14 | 0.11 ± 0.11 (*) |
| LA 500 | 0.44 | 0.15 | 1.32 | 0.27 | 1.31 | 1.10 | 0.77 ± 0.54 (***) |
| LA 1000 | 0.95 | 1.66 | 1.47 | 1.41 | 1.00 | 1.25 | 1.29 ± 0.28 (***) |
| LA 5000 | 1.31 | 1.55 | 1.56 | 1.52 | 1.40 | 1.39 | 1.46 ± 0.10 (***) |
| LA 15000 | 1.46 | 1.42 | 1.56 | 1.11 | 1.11 | 1.08 | 1.29 ± 0.21 (***) |

TABLE 14

Calcium deposition (mmol/L) in the second bone formation assay

| Group | 1 | 2 | 3 | 4 | 5 | 6 | 7 | 8 | Mean ± SD |
|-------|------|------|------|------|------|------|------|------|-----------|
| Baseline | 0 | 0.00 | 0 | 0.0 | 0 | 0 | 0.02 | 0 | 0.01 ± 0.01 |
| Control | 0.22 | 1 | 0.16 | 1 | 0.16 | 0 | 0.10 | 0.16 | 0.12 ± 0.08 (**) |
| LA 100 | 0.04 | 0.14 | 0 | 0 | 0.02 | 0.46 | 1.17 | 0 | 0.08 ± 0.11 |
| LA 500 | 0.1 | 8 | 1 | 1.5 | 1.08 | 1.63 | 1.30 | 0 | (*) |
| LA 1000 | 7 | 0.3 | 1.3 | 6 | 1.62 | 1.18 | 1.21 | 1.02 | 1.14 ± 0.55 (**) |
| LA 5000 | 1.09 | 0.8 | 1.6 | 2 | | | | 1.48 | 1.47 ± 0.20 (**) |
| | 1.7 | 1 | 4 | 1.6 | | | | | |
| LA 15000 | 0 | 1.4 | 1.2 | 8 | | | | 1.56 | 1.40 ± 0.21 (**) |
| | 1.24 | 1.46 | 2 | | | | | | |

The data shown on tables 13 and 14 were combined and analyzed. The results from table 12 were not included as there was no significant difference between the baseline and the control groups. The combined results are shown on table 15 and FIG. 4.

TABLE 15

Combined results of the effects of LA 100 -LA 15000 on bone formation activity of mature osteoblasts

| Group | number | Mean ± SD |
|-------|--------|-----------|
| Baseline | 14 | 0.01 ± 0.01 |
| Control | 14 | 0.13 ± 0.06 (***) |
| LA 100 | 14 | 0.09 ± 0.10 (**) |
| LA 500 | 14 | 0.68 ± 0.56 (***) |
| LA 1000 | 14 | 1.20 ± 0.45 (***) |
| LA 5000 | 14 | 1.47 ± 0.16 (***) |
| LA 15,000 | 14 | 1.35 ± 0.21 (***) |

Results:

All concentrations of the lanthanum (III) ion tested showed a highly significant activation of the bone formation activity of mature osteoblasts, the activation being highest with the highest test concentrations. The control substance, 17-estradiol, activated bone formation significantly.

References

Bellows C G, Aubin J E (1989) Determination of the number of osteoprogenitors in isolated fetal rat calvarial cells in vitro. Dev Biol 113:8–13.

Bellows C G, Wang Y H, Heersche J N, Aubin J E (1994) 1,25-dihydroxyvitamin $D_3$ stimulates adipocytic differentiation in cultures of fetal rat calvarial cells: comparison with the effects of dexamethasone. Endocrinology 134:2221–2229.

Friedenstein A J (1976) Precursor cells of mechanocytes. Int Rev Cytol 47:327–355.

Mundy R G (1995) Osteoblasts, bone formation and mineralization. In: Bone remodelling and its disorders. Martin Dunitz Ltd pp. 29–30.

Owen M, Friendentein A J (1988) Stromal stem cells: Marrow-derived osteogenic precursors. Ciba Found Symp 136:42–60.

Qu Q, Perälä-Heape M, Kapanen A, Dahllund J, Salo J, Väänänen H K, Harkönen, P (1998) Estrogen enhances differentiation of osteoblasts in mouse bone marrow culture. Bone 22:201–209.

Qa Q, Harkonen P L, Väänänen H K (1999) Comparative effects of oestrogen and antiestrogens on differentiation of osteoblasts in mouse bone marrow culture. J Cell Biochem 73: 500–507.

Animals for In Vitro Studies

| Species/strain/age/sex | Supplier |
| --- | --- |
| Mouse/NMRI < 8–12 w, male and female | University of Turku, The centre of experimental animals, Turku, Finland |
| Rat, Sprague-Dawley, 1 day | University of Turku, The centre of experimental animals, Turku, Finland |

Statistical Analyses of In Vitro Results

The mean and standard deviation (SD) of each group was determined. One-way analysis of variance (ANOVA) was used to study if the values obtained between different groups (baseline vs. controls and test substances) were statistically different (with p<0.05). Statistical significance is shown in each table and figure with asterisks, one asterisk (*) indicating a p-value between 0.05 and 0.01, two asterisks () a p-value between 0.01 and 0.001, and three asterisks (*) a p-value K 0.001. No asterisks indicate that the results of the group do not differ significantly from the results of the corresponding baseline group.

Summary of In Vitro Results

The effects of the test concentrations of the lanthanum (III) ion on the activity and differentiation of bone cells are summarized on table 17, where (+) means significant activation, (−) significant inhibition, and (0) no effect. One character (+ or −) means a p-value between 0.05 and 0.01, two characters (++ or −−) a p-value between 0.01 and 0.001, and three characters (+++ or −−−) a p-value <0.001.

TABLE 17

The effects of LA on bone cells

| Dose, ng/ml | Bone resorption | Osteoclast differentiation | Osteoblast differentiation | Bone formation |
| --- | --- | --- | --- | --- |
| 100 | 0 | − − | + | ++ |
| 500 | 0 | 0 | 0 | +++ |
| 1000 | 0 | − − | 0 | +++ |
| 5000 | 0 | − − − | − − − | +++ |
| 15000 | 0 | − − − | − − − | +++ |

Conclusions of In Vitro Studies

The lanthanum (III) ion is a powerful stimulator of the bone formation activity of mature osteoblasts at all concentrations tested, the best responses observed with the highest test concentrations (LA 5000 and LA 15000). However, these concentrations may also have cytotoxic effects on the osteoblast precursor cells, which may compensate the activation of mature osteoblasts in vivo.

LA 500 and LA 1000 also stimulate bone formation, but these concentrations do not decrease the formulation of osteoblasts in the osteoblast differentiation assay, suggesting that they have no cytotoxic effects on osteoblast precursor cells. However, LA 1000 decreases the formation of osteoclasts in osteoclast differentiation assay, suggesting that it may have cytotoxic effects on osteoclast precursor cells. The only significant effect of LA 500 in the four assays was the activation of bone formation. Thus, this concentration of LA may be useful in increasing the bone formation without cytotoxic effects.

LA 100 appears to activate both bone formation and osteoblast differentiation, and inhibit osteoclast differentiation and bone resorption (although the inhibition of bone resorption is not statistically significant). All these effects would strengthen bones.

EXAMPLE 5

In Vivo Bone Formation Study

Procedure:

The specimens taken from the iliac crest of growing immature dogs were analysed. The group was divided into a control and treatment group. The treatment group received 1000 mg/Kg/day of lanthanum carbonate administered orally twice daily. The groups were run for 13 weeks, after which time samples of bone were taken vertically through the iliac crest, embedded in methyl methacrylate based resin, sectioned and stained with toluidine blue and Von Kossa stain. The parameters measured were:

Trabecular and cortical bone mass

Osteoid surface and volume

Osteoblast surface

Cortical osteoid volume

Trabecular and cortical osteoclast number

Resorptive surfaces in cortex and trabecular bone

Incorporation of lanthanum within bone (modified solochrome azurine technique)

Results:

The iliac crest of these animals is acting as a growth plate. The appearances are those of immature animals actively growing. There was very active bone remodeling throughout the specimens sampled and, in addition, there appeared to be bone modelling with very active periosteal osteoclasis on the cortical surface, and within the cortex on the other.

There was a marked difference in cortical thickness between the different animals and marked variation in the amount of bone within the biopsy specimen. This degree of variation was not restricted to either of the two groups of animals, or to animals of particular sex.

There was a statistically significant difference for the trabecular bone volume between the two groups. The trabecular bone volume was lower in the control group (approximately half that in the treatment group) than in the lanthanum treated group. There was no statistically significant difference in any of the other bone parameters investigated between the two groups.

There was an increase of trabecular bone volume in treated animals (about twice) compared to the control group. These results suggest that lanthanum influences bone growth at the growth plate.

Having illustrated and described the principals of the invention in preferred embodiments, it should be appreciated to those skilled in the art that the invention can be modified in arrangement and detail without departure from such principals. We claim all modifications coming with the scope of the following claims.

All publications, patents and patent applications referred to herein are incorporated by reference in their entirety to the same extent as if each individual publication, patent or patent application was specifically and individually indicated to be incorporated by reference in its entirety.

What is claimed is:

1. A method for enhancing bone formation in a mammal in need thereof comprising administering to said mammal an effective amount of a lanthanum (III) compound, wherein said mammal has (a) a bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment, and/or (b) a bone remodeling disorder selected from the group consisting of osteoporosis, Paget's disease, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease.

2. A method according to claim 1, wherein said lanthanum (III) compound is a lanthanum carbonate.

3. A method according to claim 1, wherein said lanthanum (III) compound is a lanthanum carbonate hydrate.

4. A method according to claim 1, wherein said lanthanum (III) compound is lanthanum carbonate tetrahydrate.

5. A method according to claim 2, wherein said lanthanum (III) compound is administered in an amount of 0.01–100 mg/kg/day.

6. A method according to claim 2, wherein said lanthanum (III) compound is administered in an amount of 0.05–50 mg/kg/day.

7. A method according to claim 2, wherein said lanthanum (III) compound is administered in an amount of 0.1–10 mg/kg/day.

8. A method for enhancing bone formation in a human in need thereof comprising administering to said human an effective amount of a lanthanum (III) compound, wherein said human has (a) a bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment, and/or (b) a bone remodeling disorder selected from the group consisting of osteoporosis, Paget's disease, osteoarthritis, rheumatoid arthritis, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomaiacia and periodontal disease.

9. A method according to claim 8 wherein the human has a bone fracture, bone trauma, or a condition associated with post-traumatic bone surgery, post-prosthetic joint surgery, post-plastic bone surgery, post-dental surgery, bone chemotherapy treatment or bone radiotherapy treatment.

10. A method according to claim 8 wherein the lanthanum (III) compound is selected from the group consisting of lanthanum chloride, lanthanum carbonate, lanthanum salts, lanthanum chelates, lanthanum resins and lanthanum absorbents.

11. A method according to claim 8, wherein said lanthanum (III) compound is selected from the group consisting of lanthanum carbonate, lanthanum carbonate hydrate and lanthanum chloride.

12. A method according to claim 8 wherein the effective amount of lanthanum (III) compound is from 0.05 mg/Kg/Day to 50 mg/Kg/Day.

13. A method according to claim 12 wherein the effective amount of lanthanum (III) compound is from 0.1 mg/Kg/Day to 10 mg/Kg/Day.

14. A method according to claim 8, wherein said human has a bone remodeling disorder selected from the group consisting of osteoporosis, Paget's disease, achondroplasia, osteochodrytis, hyperparathyroidism, osteogenesis imperfecta, congenital hypophosphatasia, fribromatous lesions, fibrous displasia, multiple myeloma, abnormal bone tomover, osteolytic bone disease, osteomalacia and periodontal disease.

15. A method according to claim 14, wherein the bone remodeling disorder is osteoporosis.

16. A method according to claim 15, wherein said osteoporosis is any one of primary osteoporosis, secondary osteoporosis, post-menopausal osteoporosis, male osteoporosis and steroid induced osteoporosis.

17. A method for increasing bone density in a mammal in need thereof comprising administering to said mammal an effective amount of a lanthanum (III) compound, wherein said mammal has (a) a bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment, and/or (b) a bone remodeling disorder selected from the group consisting of osteoporosis, Paget's disease, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease.

18. A method according to claim 17, wherein said lanthanum (III) compound is a lanthanum carbonate.

19. A method for increasing bone density in a human in need thereof comprising administering to said human an effective amount of a lanthanum (III) compound, wherein said mammal has (a) a bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment, and/or (b) a bone remodeling disorder selected from the group consisting of osteoporosis, Paget's disease, osteoarthritis, rheumatoid arthritis, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease.

20. A method according to claim 19, said wherein lanthanum (III) compound is selected from the group consisting of lanthanum carbonate, lanthanum carbonate hydrate and lanthanum chloride.

21. A method for stimulating osteoblast differentiation in a mammal in need thereof comprising administering to said mammal and contacting said osteoblasts with an effective amount of lanthanum (III) compound thereby stimulating differentiation, wherein said mammal has (a) a bone fracture, bone trauma, or a bone deficit condition associated with post-traumatic bone surgery, post-prosthetic joint surgery, post-plastic bone surgery, past-dental surgery, bone chemotherapy treatment or bone radiotherapy treatment, and/or (b) a bone remodeling disorder selected from the group consisting of osteoporosis, Paget's disease, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease.

22. A method according to claim 21, wherein said lanthanum (III) compound is a lanthanum carbonate.

23. A method for stimulating osteoblast differentiation in a human in need thereof comprising administering to said human and contacting said osteoblasts with an effective amount of lanthanum (III) compound thereby stimulating differentiation, wherein said mammal has (a) a bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment, and/or (b) a bone remodeling disorder selected from the group consisting of osteoporosis, Paget's disease, osteoarthritis, rheumatoid arthritis, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease.

24. A method according to claim 23, said wherein lanthanum (III) compound is selected from the group consisting of lanthanum carbonate, lanthanum carbonate hydrate and lanthanum chloride.

25. A method for inhibiting osteoclast differentiation in a mammal in need thereof comprising administering to said mammal and contacting said osteoclasts with an effective amount of lanthanum (III) compound thereby inhibiting differentiation, wherein said mammal has (a) a bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment, and/or (b) a bone remodeling disorder selected from the group consisting of osteoporosis, Paget's disease, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease.

26. A method according to claim 25, wherein said lanthanum (III) compound is a lanthanum carbonate.

27. A method for inhibiting osteoclast differentiation in a human in need thereof comprising administering to said human and contacting said osteoclasts with an effective amount of lanthanum (III) compound thereby inhibiting differentiation, wherein said mammal has (a) a bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment, and/or (b) a bone remodeling disorder selected from the group consisting of osteoporosis, Paget's disease, osteoarthritis, rheumatoid arthritis, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease.

28. A method according to claim 27, said wherein lanthanum (III) compound is selected from the group consisting of lanthanum carbonate, lanthanum carbonate hydrate and lanthanum chloride.

29. A method for activating bone formation activity of differentiated osteoblasts in a mammal in need thereof comprising administering to said mammal and contacting said osteoblasts with an effective amount of lanthanum (III) compound thereby stimulating bone formation, wherein said mammal has (a) a bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment, and/or (b) a bone remodeling disorder selected from the group consisting of osteoporosis, Paget's disease, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease.

30. A method according to claim 29, wherein said lanthanum (III) compound is a lanthanum carbonate.

31. A method for activating bone formation activity of differentiated osteoblasts in a human in need thereof comprising administering to said human and contacting said osteoblasts with an effective amount of lanthanum (III) compound thereby stimulating bone formation, wherein said mammal has (a) a bone fracture, hone trauma, or a bone deficit condition associated with post-traumatic bone surgery, post-prosthetic joint surgery, post-plastic bone surgery, post-dental surgery, bone chemotherapy treatment or bone radiotherapy treatment, and/or (b) a bone remodeling disorder selected from the group consisting of osteoporosis, Paget's disease, osteoarthritis, rheumatoid arthritis, achondroplasia, osteochodrytis, hyperparathyroidism, osteogenesis imperfecta, congenital hypophosphatasia, fibromatous lesions, fibrous displasia; multiple myeloma, abnormal bone turnover, osteolytic bone disease, osteomalacia and periodontal disease.

32. A method according to claim 31, said wherein lanthanum (III) compound is selected from the group consisting of lanthanum carbonate, lanthanum carbonate hydrate and lanthanum chloride.

33. A method for simultaneously stimulating osteoblast differentiation and inhibiting osteoclast differentiation in a mammal having a bone remodeling disorder selected from the group consisting of osteoporosis, Paget's disease, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease comprising administering to said mammal an effective amount of lanthanum (III) compound.

34. A method according to claim 33, wherein said lanthanum (III) compound is a lanthanum carbonate.

35. A method for simultaneously stimulating osteoblast differentiation and inhibiting osteoclast differentiation in a human having a bone remodeling disorder selected from the group consisting of osteoporosis, Paget's disease, osteoarthritis, rheumatoid arthritis, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease comprising administering to said human an effective amount of lanthanum (III) compound.

36. A method according to claim 35, said wherein lanthanum (III) compound is selected from the group consisting of lanthanum carbonate, lanthanum carbonate hydrate and lanthanum chloride.

37. A method for enhancing bone formation in a mammal in need thereof comprising administering to said mammal an effective amount of a lanthanum (III) compound and at least one bone enhancing agent.

38. A method according to claim 37 wherein said bone enhancing agent is selected from the group consisting of a synthetic hormone, a natural hormone, oestrogen, calcitonin, tamoxifen, a biphosphonate, a biphosphonate analog, vitamin D, a vitamin D analog, a mineral supplement, a statin drug, a selective oestrogen receptor modulator and sodium fluoride.

39. A method according to claim 37, wherein said lanthanum (III) compound is a lanthanum carbonate.

40. A method for inhibiting osteoclastic differentiation whereby to manage or treat a bone disease which comprises administering to a human or animal subject suffering from said bone disease, wherein said disease is not osteoarthritis or rheumatoid arthritis, a therapeutically effective amount of a lanthanum (III) compound.

41. A method according to claim 40, wherein said lanthanum (III) compound is a lanthanum carbonate.

42. A method for activating osteoblastic differentiation whereby to manage or treat a bone disease which comprises administering to a human or animal subject mattering from said bone disease, wherein said disease is not osteoarthritis or rheumatoid arthritis, a therapeutically effective amount of a lanthanum (III) compound and activating osreoblastic differentiation.

43. A method according to ciaim 42, wherein said lanthanum (III) compound is a lanthanum carbonate.

44. A method for enhancing bone formation in a mammal in need thereof comprising administering to said mammal an effective amount of a lanthanum (III) compound, wherein said mammal has (a) a bone fracture, bone trauma, or a bone deficit condition associated with post-traumatic bone surgery, past-prosthetic joint surgery, post-plastic bone surgery, post-dental surgery, bone chemotherapy treatment or bone radiotherapy treatment, and/or (b) a bone remodeling disorder selected from the group consisting of osteoporosis, Paget's disease, osteoarthritis, rheumatoid arthritis, achondroplasia, osteochodrytis, hyperparathyroidism, osteogenesis imperfecta, congenital hypophosphatasia, fibromatous lesions, fibrous displasia, multiple myeloma, abnormal bone turnover, osteolytic bone disease, osteomalacia and periodontal disease, wherein said lanthanum (III) compound is not a chelate.

* * * * *

UNITED STATES PATENT AND TRADEMARK OFFICE
CERTIFICATE OF CORRECTION

PATENT NO.         : 7,078,059 B2
APPLICATION NO. : 09/891206
DATED              : July 18, 2006
INVENTOR(S)        : Nigel D. Atherton et al.

Page 1 of 1

It is certified that error appears in the above-identified patent and that said Letters Patent is hereby corrected as shown below:

On the title page, item [75]:

Please delete "Joseph William Totten, Hampshire (GB)", and substitute

-- Joseph W. Totten, Hampshire (GB) --.

Signed and Sealed this

Twenty-eighth Day of November, 2006

JON W. DUDAS
*Director of the United States Patent and Trademark Office*